(12) United States Patent
Kulig et al.

(10) Patent No.: US 11,440,878 B2
(45) Date of Patent: *Sep. 13, 2022

(54) FUNCTIONAL DISULFIDE VEGETABLE OILS, METHOD OF MAKING AND USE IN RUBBER COMPOSITIONS AND TIRES

(71) Applicant: The Goodyear Tire & Rubber Company, Akron, OH (US)

(72) Inventors: Joseph John Kulig, Tallmadge, OH (US); Kelsey Elizabeth Cantwell, Akron, OH (US); Frank James Feher, Copley, OH (US); Thomas Franklin Spilker, Broadview Heights, OH (US); George Jim Papakonstantopoulos, Medina, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 99 days.

This patent is subject to a terminal disclaimer.

(21) Appl. No.: 16/671,285

(22) Filed: Nov. 1, 2019

(65) Prior Publication Data

US 2021/0130287 A1 May 6, 2021

(51) Int. Cl.
| | |
|---|---|
| *C07C 323/52* | (2006.01) |
| *C08L 91/02* | (2006.01) |
| *C07C 323/54* | (2006.01) |
| *C08L 9/00* | (2006.01) |
| *C08L 9/06* | (2006.01) |
| *C07C 321/12* | (2006.01) |
| *C07C 319/18* | (2006.01) |
| *C07C 321/18* | (2006.01) |
| *B60C 1/00* | (2006.01) |

(52) U.S. Cl.
CPC .......... *C07C 323/52* (2013.01); *C07C 319/18* (2013.01); *C07C 321/12* (2013.01); *C07C 321/18* (2013.01); *C07C 323/54* (2013.01); *C08L 9/00* (2013.01); *C08L 9/06* (2013.01); *C08L 91/02* (2013.01); *B60C 1/00* (2013.01)

(58) Field of Classification Search
CPC ... C07C 323/52; C07C 323/54; C07C 319/18; C07C 321/12; C07C 321/18
See application file for complete search history.

(56) References Cited

U.S. PATENT DOCUMENTS

| | | | |
|---|---|---|---|
| 3,476,826 A | 11/1969 | Millen | |
| 4,039,586 A | 8/1977 | Shasha et al. | |
| 4,512,926 A | 4/1985 | Kampf et al. | |
| 5,395,891 A | 3/1995 | Obrecht et al. | |
| 5,512,190 A | 4/1996 | Anderson et al. | |
| 5,672,639 A | 9/1997 | Corvasce et al. | |
| 6,127,488 A | 10/2000 | Obrecht et al. | |
| 6,133,364 A | 10/2000 | Obrecht et al. | |
| 6,207,757 B1 | 3/2001 | Obrecht et al. | |
| 6,242,534 B1 | 6/2001 | Obrecht et al. | |
| 6,359,046 B1 | 3/2002 | Cruse | |
| 6,372,857 B1 | 4/2002 | Obrecht et al. | |
| 6,608,125 B2 | 8/2003 | Cruse et al. | |
| 7,521,401 B2 | 4/2009 | Rowland | |
| 9,238,588 B2 | 1/2016 | Harrington et al. | |
| 9,550,850 B2 | 1/2017 | Sato et al. | |
| 10,005,857 B2 | 6/2018 | Kloppenburg et al. | |
| 10,245,234 B1 | 4/2019 | Lele | |
| 2003/0130535 A1 | 7/2003 | Deschler et al. | |
| 2006/0235120 A1 | 10/2006 | Saiki et al. | |
| 2009/0076279 A1 | 3/2009 | Rowland et al. | |
| 2009/0292054 A1 | 11/2009 | Omura et al. | |
| 2010/0083871 A1 | 4/2010 | Narayan et al. | |
| 2012/0064322 A1* | 3/2012 | Upshaw | C08L 61/20 428/220 |
| 2014/0335032 A1 | 11/2014 | Panandiker et al. | |
| 2014/0335167 A1 | 11/2014 | Panandiker et al. | |
| 2015/0166701 A1 | 6/2015 | Chisholm et al. | |
| 2020/0377702 A1 | 12/2020 | Schoeffel et al. | |

FOREIGN PATENT DOCUMENTS

| | | |
|---|---|---|
| CN | 105713700 B | 8/2018 |
| GB | 455779 A | 10/1936 |
| JP | 2014177431 A | 9/2014 |

OTHER PUBLICATIONS

Bhaumik et al., Rapid Transformation of Alkyl Halides into Symmetrical Disulfides Using Sodium Sulfide and Carbon Disulfide, SynOpen, 1, 2017, pp. 117-120, Georg Thieme Verlag Stuttgart, New York.

Ionescu et al., Functionalized vegetable oils as precursors for polymers by thiol-ene reaction, European Polymer Journal 67, 2015, pp. 439-448, Elsevier Ltd.

Kuhlmann et al., Cysteine-Functional Polymers via Thiol-ene Conjugation, Macromol. Rapid Commun., 2015, 472-476, 36, WILEY-VCH Verlag GmbH & Co. KGaA, Weinheim.

Li et al., Modified soybean oil-extended SBR compounds and vulcanizates filled with carbon black, Polymer, Jan. 13, 2015, pp. 144-156, 60, Elsevier Ltd.

Mehta et al., Moderate Temperature Curing of Plant Oils with Bismaleimides via the Ene Reaction, Ind. Eng. Chem. Res., Oct. 13, 2016, https://pubs.acs.org/doi/pdf/10.1021/acs.iecr.6b03004, 55, 45, American Chemical Society.

Nalawade et al., Modified soybean oil as a reactive diluent: coating performance, Journal of Coatings Technology and Research, Jun. 11, 2015, pp. 1005-1021, 12, American Coatings Association.

Nalawade et al., Modified soybean oil as a reactive diluent: Synthesis and characterization, Polymer Chemistry, Aug. 24, 2014, Journal of Polymer Science.

Shibata et al., High Performance Bio-Based Thermosetting Resins Composed of Tung Oil and Bismaleimide, Journal of Applied Polymer Science, Feb. 5, 2010, pp. 896-901, 119(2), Wiley Periodicals, Inc.

(Continued)

*Primary Examiner* — Patrick D Niland
(74) *Attorney, Agent, or Firm* — Mandy B. Willis; John D. DeLong

(57) ABSTRACT

The present invention is directed to novel functionalized vegetable oils, a method of making the oils, their use in rubber compositions, and their use in tires.

17 Claims, No Drawings

(56) References Cited

OTHER PUBLICATIONS

Shibata et al., High-performance bio-based bismaleimide resins using succinic acid and eugenol, Polymer Journal, Sep. 14, 2011, pp. 916-922, 43, The Society of Polymer Science, Japan.

Yoon et al., Self-Healing Polymer Films Based on Thiol-Disulfide Exchange Reactions and Self-Healing Kinetics Measured Using Atomic Force Microscopy, Macromolecules, Dec. 16, 2011, pp. 142-149, 45, 1, American Chemical Society.

Tambe Chetan el al, Silylation of Non-Terminal Double Bonds of Natural Oils, Silylation of Non-Terminal Double Bonds of Natural Oils, Jun. 12, 2015 (Jun. 12, 2015), 87-98, vol. 8, No. 1, Silicon, East Lansing, US.

European Search Report for Serial No. EP20204383 dated May 3, 2021.

* cited by examiner

FUNCTIONAL DISULFIDE VEGETABLE OILS, METHOD OF MAKING AND USE IN RUBBER COMPOSITIONS AND TIRES

BACKGROUND

Heretofore, although progress in the elastomer field has improved to such an extent that synthetic elastomers have supplemented or replaced natural rubber to a large extent in the fabrication of tires or other rubber products, synthetic elastomers still generally exhibit low green strength. This is true even for synthetic cis-1,4-polyisoprene. By the term "green strength" it is generally meant that property of a polymer or elastomer common in natural rubber, which contributes to the proper building conditions where multiple components are employed and which result in little or undesirable relative movement of the assembled components subsequent to assembly and prior to initiation of the curing operation. Generally, green strength is measured by stress-strain measurements.

There remains a need for ways to improve the green strength in curable rubber compounds.

SUMMARY

The present invention is directed to a vegetable oil derivative comprising the structure

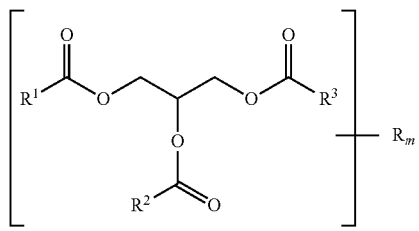

where $R^1$, $R^2$ and $R^3$ are independently C15-C20 alkenyl, C15-C20 alkyl, and optionally containing aromatic groups; R is —S—S—$R^4$ or R is —S—X—S—S—$R^4$ where X is substituted or unsubstituted alkane diyl, substituted or unsubstituted phenylene, or a combination thereof; $R^4$ is a monovalent organic group; each R is covalently bonded to a carbon atom of one of $R^1$, $R^2$ or $R^3$; and m is the number of R groups.

The invention is further directed to a method of making the vegetable oil derivative, a rubber composition and a pneumatic tire.

DESCRIPTION

There is disclosed a vegetable oil derivative

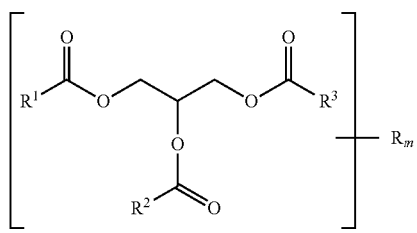

where $R^1$, $R^2$ and $R^3$ are independently C15-C20 alkenyl, C15-C20 alkyl, and optionally containing aromatic groups; R is —S—S—$R^4$ or R is —S—X—S—S—$R^4$ where X is substituted or unsubstituted alkane diyl, substituted or unsubstituted phenylene, or a combination thereof; $R^4$ is a monovalent organic group; each R is covalently bonded to a carbon atom of one of $R^1$, $R^2$ or $R^3$; and m is the number of R groups.

The vegetable oil derivative may be produced by modification of a triglyceride.

In various embodiments, the vegetable oil derivative may be produced via disulfide exchange with modified triglyceride containing at least one thiol group (—SH, also known as mercapto or sulfanyl,) otherwise referred to herein as a thiolized or mercaptanized triglyceride.

Triglyceride starting material has the general structure

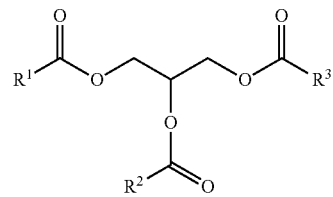

where $R^1$, $R^2$, and $R^3$ are as defined previously. Suitable triglycerides include vegetable oils and their derivatives, preferably soybean oil. One or more of groups $R^1$, $R^2$, and $R^3$ must contain at least one olefin bond.

In one embodiment, the triglyceride is a vegetable oil. Suitable vegetable oils include those with olefinic unsaturation in their fatty acid chains, including but not limited to soybean oils, canola oils, castor oils, palm oils, coconut oil, and corn oils. In one embodiment, the triglyceride is a high oleic soybean oil, containing about 75 percent by weight of oleic acid residues as oleyl chains.

In one embodiment, the thiolized triglyceride is produced via a thiol-ene reaction of a dithiol with the triglyceride. For the thiol-ene reaction, dithiols are used of the general structure

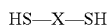

HS—X—SH

HS-Q-SH where Q is substituted or unsubstituted alkane diyl, substituted or unsubstituted phenylene, or a combination thereof, including substructures containing other functionalities, including alcohols, carbonyls, carboxylic acids, esters, anhydrides, amines, amides, amino acids, imines, or halides. In one embodiment, the dithiol is of the structure

HS—$(CH_2)_n$—SH where n=1-12, preferably 3-6, and most preferably 6. Reaction of the dithiol with the triglyceride provides free thiol functionality on the thiol-modified triglyceride for subsequent reactivity.

The thiol-ene reaction between a dithiol and olefinic unsaturation of the triglyceride to produce a thiolized triglyceride may proceed as follows

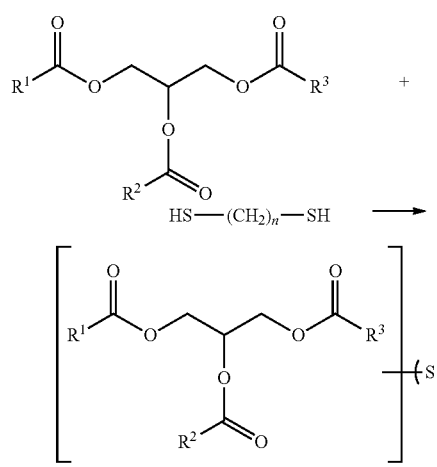

where m is the number of dithiol residues covalently bonded to a carbon atom of one of $R^1$, $R^2$ or $R^3$ resulting from the thiol-ene reaction. The olefin-containing triglyceride may be partially or fully functionalized with free thiols via thiol-ene reaction, depending on the reaction conditions to give the general structure above of a thiolized triglyceride.

Alternatively, the thiolized triglyceride is produced via direct addition of $H_2S$ to the triglyceride to produce a mercaptanized triglyceride:

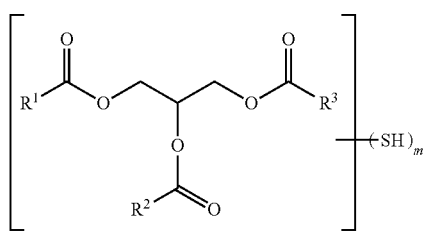

where each thiol group —SH is covalently bonded to a carbon atom of one of $R^1$, $R^2$ or $R^3$. In one embodiment, the thiolized triglyceride is a mercaptanized soybean oil such as that commercially available as Polymercaptan 358 from Chevron Phillips.

Disulfides of the general formula

may be used in a disulfide exchange reaction with the modified triglyceride containing at least one thiol group to produce a disulfidic triglyceride having a further functionality. In one embodiment, the thiolized triglyceride resulting from reaction of a triglyceride with a dithiol may be used in a disulfide exchange as follows:

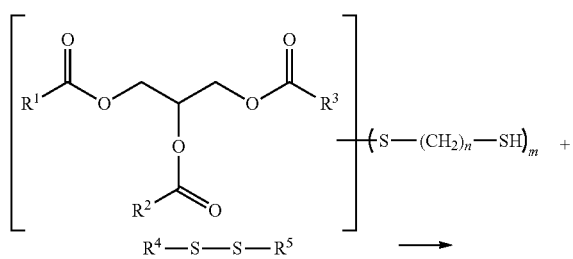

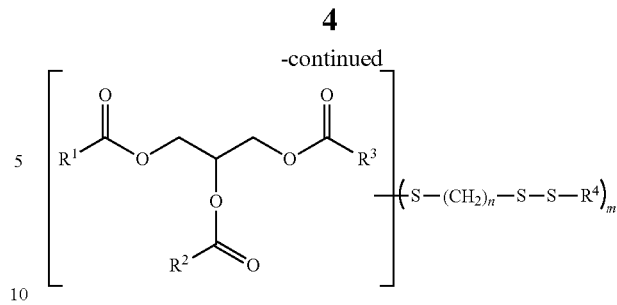

In another embodiment, the thiolized triglyceride resulting from reaction of a triglyceride with $H_2S$ may be used in a disulfide exchange as follows:

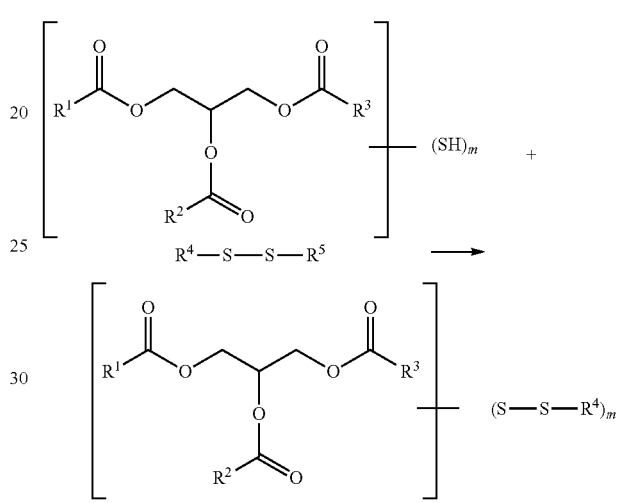

Such disulfidic triglyceride may be a vegetable oil derivative in embodiments where the triglyceride is a vegetable oil.

Suitable disulfides $R^4$—S—S—$R^5$ may be either symmetric or asymmetric. $R^5$ must be a good leaving group, such that if $R^4$=$R^5$, a stable byproduct is formed, preferably benzothiazole. $R^4$ may be any monovalent organic group. In one embodiment, $R^4$ is a sulfur-containing group capable of accelerating sulfur vulcanization. In one embodiment, the disulfide is selected from mercaptobenzothiazole disulfide (2,2'-dithiobisbenzothiazole), a thiuram disulfide such as tetramethyl thiuram disulfide, tetraethyl thiuram disulfide, tetrabutyl thiuram disulfide, dipentamethylenethiuram disulfide, and N, N'-dimethyl-N, N'-diphenylthiuram disulfide. In one embodiment, $R^4$ may be selected from the following structures

where Z is a group that helps control the reactivity of the thiocarbonylthio moiety;

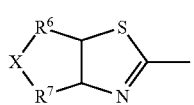

where X=0-2 carbon atoms; $R^6$, $R^7$ can be independently hydrogen, alkyl chains, or aromatic moieties;

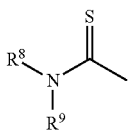

where $R^8$, $R^9$ can be independently alkyl or aromatic functionalities;

$R^{10}$— where $R^{10}$ is a substituted or non-substituted aromatic heterocycle;

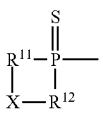

where X=0-2 carbon atoms; $R^{11}$, $R^{12}$ can be symmetric or asymmetric and independently be an alkyl, aromatic, or ethereal substituents;

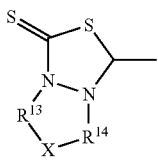

where X=0-2 carbon atoms; $R^{13}$, $R^{14}$ can be symmetric or asymmetric and are independently hydrogen, an alkyl chain, aromatic containing functional group;

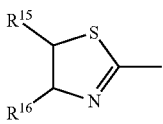

where $R^{15}$, $R^{16}$ can be independently hydrogen, alkyl chains, or aromatic moieties.

In one embodiment, the functional oil is a soybean oil functionalized with mercaptobenzothiazole disulfide, where the disulfide content can vary from 1-8 substituents per triglyceride molecule.

The vegetable oil derivative may be used in a vulcanizable rubber composition. In one embodiment, the vegetable oil derivative is used in an amount ranging from 1 to 80 phr.

The rubber composition may include, in addition to the vegetable oil derivative, one or more rubbers or elastomers containing olefinic unsaturation. The phrases "rubber or elastomer containing olefinic unsaturation" or "diene based elastomer" are intended to include both natural rubber and its various raw and reclaim forms as well as various synthetic rubbers. In the description of this invention, the terms "rubber" and "elastomer" may be used interchangeably, unless otherwise prescribed. The terms "rubber composition," "compounded rubber" and "rubber compound" are used interchangeably to refer to rubber which has been blended or mixed with various ingredients and materials and such terms are well known to those having skill in the rubber mixing or rubber compounding art. Representative synthetic polymers are the homopolymerization products of butadiene and its homologues and derivatives, for example, methylbutadiene, dimethylbutadiene and pentadiene as well as copolymers such as those formed from butadiene or its homologues or derivatives with other unsaturated monomers. Among the latter are acetylenes, for example, vinyl acetylene; olefins, for example, isobutylene, which copolymerizes with isoprene to form butyl rubber; vinyl compounds, for example, acrylic acid, acrylonitrile (which polymerize with butadiene to form NBR), methacrylic acid and styrene, the latter compound polymerizing with butadiene to form SBR, as well as vinyl esters and various unsaturated aldehydes, ketones and ethers, e.g., acrolein, methyl isopropenyl ketone and vinylethyl ether. Specific examples of synthetic rubbers include neoprene (polychloroprene), polybutadiene (including cis-1,4-polybutadiene), polyisoprene (including cis-1,4-polyisoprene), butyl rubber, halobutyl rubber such as chlorobutyl rubber or bromobutyl rubber, styrene/isoprene/butadiene rubber, copolymers of 1,3-butadiene or isoprene with monomers such as styrene, acrylonitrile and methyl methacrylate, as well as ethylene/propylene terpolymers, also known as ethylene/propylene/diene monomer (EPDM), and in particular, ethylene/propylene/dicyclopentadiene terpolymers. Additional examples of rubbers which may be used include alkoxy-silyl end functionalized solution polymerized polymers (SBR, PBR, IBR and SIBR), silicon-coupled and tin-coupled star-branched polymers. The preferred rubber or elastomers are polyisoprene (natural or synthetic), polybutadiene and SBR.

In one aspect the at least one additional rubber is preferably of at least two of diene based rubbers. For example, a combination of two or more rubbers is preferred such as cis 1,4-polyisoprene rubber (natural or synthetic, although natural is preferred), 3,4-polyisoprene rubber, styrene/isoprene/butadiene rubber, emulsion and solution polymerization derived styrene/butadiene rubbers, cis 1,4-polybutadiene rubbers and emulsion polymerization prepared butadiene/acrylonitrile copolymers.

In one aspect of this invention, an emulsion polymerization derived styrene/butadiene (E-SBR) might be used having a relatively conventional styrene content of about 20 to about 28 percent bound styrene or, for some applications, an E-SBR having a medium to relatively high bound styrene content, namely, a bound styrene content of about 30 to about 45 percent.

By emulsion polymerization prepared E-SBR, it is meant that styrene and 1,3-butadiene are copolymerized as an aqueous emulsion. Such are well known to those skilled in such art. The bound styrene content can vary, for example, from about 5 to about 50 percent. In one aspect, the E-SBR may also contain acrylonitrile to form a terpolymer rubber, as E-SBAR, in amounts, for example, of about 2 to about 30 weight percent bound acrylonitrile in the terpolymer.

Emulsion polymerization prepared styrene/butadiene/acrylonitrile copolymer rubbers containing about 2 to about 40 weight percent bound acrylonitrile in the copolymer are also contemplated as diene based rubbers for use in this invention.

The solution polymerization prepared SBR (S-SBR) typically has a bound styrene content in a range of about 5 to about 50, preferably about 9 to about 36, percent. The S-SBR can be conveniently prepared, for example, by organo lithium catalyzation in the presence of an organic hydrocarbon solvent.

In one embodiment, cis 1,4-polybutadiene rubber (BR) may be used. Such BR can be prepared, for example, by organic solution polymerization of 1,3-butadiene. The BR may be conveniently characterized, for example, by having at least a 90 percent cis 1,4-content.

The cis 1,4-polyisoprene and cis 1,4-polyisoprene natural rubber are well known to those having skill in the rubber art.

The term "phr" as used herein, and according to conventional practice, refers to "parts by weight of a respective material per 100 parts by weight of rubber, or elastomer."

The rubber composition may also include up to 70 phr of processing oil. Processing oil may be included in the rubber composition as extending oil typically used to extend elastomers. Processing oil may also be included in the rubber composition by addition of the oil directly during rubber compounding. The processing oil used may include both extending oil present in the elastomers, and process oil added during compounding. Suitable process oils include various oils as are known in the art, including aromatic, paraffinic, naphthenic, vegetable oils, and low PCA oils, such as MES, TDAE, SRAE and heavy naphthenic oils. Suitable low PCA oils include those having a polycyclic aromatic content of less than 3 percent by weight as determined by the IP346 method. Procedures for the IP346 method may be found in *Standard Methods for Analysis & Testing of Petroleum and Related Products* and *British Standard* 2000 *Parts,* 2003, 62nd edition, published by the Institute of Petroleum, United Kingdom.

The rubber composition may include from about 10 to about 150 phr of silica. In another embodiment, from 20 to 80 phr of silica may be used.

The commonly employed siliceous pigments which may be used in the rubber compound include conventional pyrogenic and precipitated siliceous pigments (silica). In one embodiment, precipitated silica is used. The conventional siliceous pigments employed in this invention are precipitated silicas such as, for example, those obtained by the acidification of a soluble silicate, e.g., sodium silicate.

Such conventional silicas might be characterized, for example, by having a BET surface area, as measured using nitrogen gas. In one embodiment, the BET surface area may be in the range of about 40 to about 600 square meters per gram. In another embodiment, the BET surface area may be in a range of about 80 to about 300 square meters per gram. The BET method of measuring surface area is described in the *Journal of the American Chemical Society*, Volume 60, Page 304 (1930).

The conventional silica may also be characterized by having a dibutylphthalate (DBP) absorption value in a range of about 100 to about 400, alternatively about 150 to about 300.

The conventional silica might be expected to have an average ultimate particle size, for example, in the range of 0.01 to 0.05 micron as determined by the electron microscope, although the silica particles may be even smaller, or possibly larger, in size.

Various commercially available silicas may be used, such as, only for example herein, and without limitation, silicas commercially available from PPG Industries under the Hi-Sil trademark with designations 210, 243, etc; silicas available from Rhodia, with, for example, designations of Z1165MP and Z165GR and silicas available from Degussa AG with, for example, designations VN2 and VN3, etc.

Commonly employed carbon blacks can be used as a conventional filler in an amount ranging from 10 to 150 phr. In another embodiment, from 20 to 80 phr of carbon black may be used. Representative examples of such carbon blacks include N110, N121, N134, N220, N231, N234, N242, N293, N299, N315, N326, N330, N332, N339, N343, N347, N351, N358, N375, N539, N550, N582, N630, N642, N650, N683, N754, N762, N765, N774, N787, N907, N908, N990 and N991. These carbon blacks have iodine absorptions ranging from 9 to 145 g/kg and DBP number ranging from 34 to 150 cm$^3$/100 g.

Other fillers may be used in the rubber composition including, but not limited to, particulate fillers including ultra-high molecular weight polyethylene (UHMWPE), crosslinked particulate polymer gels including but not limited to those disclosed in U.S. Pat. No. 6,242,534; 6,207,757; 6,133,364; 6,372,857; 5,395,891; or 6,127,488, and plasticized starch composite filler including but not limited to that disclosed in U.S. Pat. No. 5,672,639. Such other fillers may be used in an amount ranging from 1 to 30 phr.

In one embodiment, the rubber composition may contain a conventional sulfur containing organosilicon compound. In one embodiment, the sulfur containing organosilicon compounds are the 3,3'-bis(trimethoxy or triethoxy silylpropyl) polysulfides. In one embodiment, the sulfur containing organosilicon compounds are 3,3'-bis(triethoxysilylpropyl) disulfide and/or 3,3'-bis(triethoxysilylpropyl) tetrasulfide.

In another embodiment, suitable sulfur containing organosilicon compounds include compounds disclosed in U.S. Pat. No. 6,608,125. In one embodiment, the sulfur containing organosilicon compounds includes 3-(octanoylthio)-1-propyltriethoxysilane, $CH_3(CH_2)_6C(=O)-S-CH_2CH_2CH_2Si(OCH_2CH_3)_3$, which is available commercially as NXT™ from Momentive Performance Materials.

In another embodiment, suitable sulfur containing organosilicon compounds include those disclosed in U.S. Patent Publication No. 2003/0130535. In one embodiment, the sulfur containing organosilicon compound is Si-363 from Degussa.

The amount of the sulfur containing organosilicon compound in a rubber composition will vary depending on the level of other additives that are used. Generally speaking, the amount of the compound will range from 0.5 to 20 phr. In one embodiment, the amount will range from 1 to 10 phr.

It is readily understood by those having skill in the art that the rubber composition would be compounded by methods generally known in the rubber compounding art, such as mixing the various sulfur-vulcanizable constituent rubbers with various commonly used additive materials such as, for example, sulfur donors, curing aids, such as activators and retarders and processing additives, such as oils, resins including tackifying resins and plasticizers, fillers, pigments, fatty acid, zinc oxide, waxes, antioxidants and antiozonants and peptizing agents. As known to those skilled in the art, depending on the intended use of the sulfur vulcanizable and sulfur-vulcanized material (rubbers), the additives mentioned above are selected and commonly used in conventional amounts. Representative examples of sulfur donors include elemental sulfur (free sulfur), an amine disulfide, polymeric polysulfide and sulfur olefin adducts. In one embodiment, the sulfur-vulcanizing agent is elemental sulfur. The sulfur-vulcanizing agent may be used in an amount ranging from 0.5 to 8 phr, alternatively with a range of from 1.5 to 6 phr. Typical amounts of tackifier resins, if used, comprise about 0.5 to about 10 phr, usually about 1 to about 5 phr. Typical amounts of processing aids comprise about 1 to about 50 phr. Typical amounts of antioxidants comprise about 1 to about 5 phr. Representative antioxidants may be, for example, diphenyl-p-phenylenediamine and others, such as, for example, those disclosed in *The Vanderbilt Rubber Handbook* (1978), Pages 344 through 346. Typical amounts of antiozonants comprise about 1 to 5 phr. Typical amounts of fatty acids, if used, which can include stearic acid comprise about 0.5 to about 3 phr. Typical amounts of zinc oxide comprise about 2 to about 5 phr. Typical amounts of waxes comprise about 1 to about 5 phr. Often microcrystalline waxes are used. Typical amounts of peptizers comprise about 0.1 to about 1 phr. Typical peptizers may be, for example, pentachlorothiophenol and dibenzamidodiphenyl disulfide.

Accelerators are used to control the time and/or temperature required for vulcanization and to improve the properties of the vulcanizate. In one embodiment, a single accelerator system may be used, i.e., primary accelerator. The primary accelerator(s) may be used in total amounts ranging from about 0.5 to about 4, alternatively about 0.8 to about 1.5, phr. In another embodiment, combinations of a primary and a secondary accelerator might be used with the secondary accelerator being used in smaller amounts, such as from about 0.05 to about 3 phr, in order to activate and to improve the properties of the vulcanizate. Combinations of these accelerators might be expected to produce a synergistic effect on the final properties and are somewhat better than those produced by use of either accelerator alone. In addition, delayed action accelerators may be used which are not affected by normal processing temperatures but produce a satisfactory cure at ordinary vulcanization temperatures. Vulcanization retarders might also be used. Suitable types of accelerators that may be used in the present invention are amines, disulfides, guanidines, thioureas, thiazoles, thiurams, sulfenamides, dithiocarbamates and xanthates. In one embodiment, the primary accelerator is a sulfenamide. If a second accelerator is used, the secondary accelerator may be a guanidine, dithiocarbamate or thiuram compound.

The mixing of the rubber composition can be accomplished by methods known to those having skill in the rubber mixing art. For example, the ingredients are typically mixed in at least two stages, namely, at least one non-productive stage followed by a productive mix stage. The final curatives including sulfur-vulcanizing agents are typically mixed in the final stage which is conventionally called the "productive" mix stage in which the mixing typically occurs at a temperature, or ultimate temperature, lower than the mix temperature(s) than the preceding non-productive mix stage(s). The terms "non-productive" and "productive" mix stages are well known to those having skill in the rubber mixing art. The rubber composition may be subjected to a thermomechanical mixing step. The thermomechanical mixing step generally comprises a mechanical working in a mixer or extruder for a period of time suitable in order to produce a rubber temperature between 140° C. and 190° C. The appropriate duration of the thermomechanical working varies as a function of the operating conditions, and the volume and nature of the components. For example, the thermomechanical working may be from 1 to 20 minutes.

The rubber composition may be incorporated in a variety of rubber components of the tire. For example, the rubber component may be a tread (including tread cap and tread base), sidewall, apex, chafer, sidewall insert, wirecoat or innerliner. In one embodiment, the component is a tread.

Alternatively, the rubber composition may be used in various manufactured items including but not limited to tire treads, shoes, shoe soles, transmission belts, hoses, airsprings, conveyor belts, track belts, and vibration isolators.

The pneumatic tire of the present invention may be a race tire, passenger tire, aircraft tire, agricultural, earthmover, off-the-road, truck tire, and the like. In one embodiment, the tire is a passenger or truck tire. The tire may also be a radial or bias.

Vulcanization of the pneumatic tire of the present invention is generally carried out at conventional temperatures ranging from about 100° C. to 200° C. In one embodiment, the vulcanization is conducted at temperatures ranging from about 110° C. to 180° C. Any of the usual vulcanization processes may be used such as heating in a press or mold, heating with superheated steam or hot air. Such tires can be built, shaped, molded and cured by various methods which are known and will be readily apparent to those having skill in such art.

This invention is illustrated by the following examples that are merely for the purpose of illustration and are not to be regarded as limiting the scope of the invention or the manner in which it can be practiced. Unless specifically indicated otherwise, parts and percentages are given by weight.

EXAMPLES

General Experimental

For internal illumination: A glass UV reactor was used for photocatalytic thiol-ene reactions. The reactor was equipped with a water-cooled, jacketed internal illumination well. The light source was a medium pressure, Hg vapor lamp. The Hg lamp was fitted with a Pyrex Absorp Sleeve to eliminate wavelengths below ~300 nm.

For external illumination: A glass bottle was used for photocatalytic thiol-ene reactions. The light source was a medium pressure, Hg vapor lamp. The Hg lamp was fitted with a Pyrex Absorp Sleeve to eliminate wavelengths below ~300 nm. The light source was placed inside a water-cooled, jacketed illumination well, which was then positioned adjacent to the bottle during the reaction to allow for full illumination.

Example 1. Synthesis of HOSBO-HDT$_2$

High oleic soybean oil (200 g, 0.227 mol), 1,6-hexanedithiol (3 eq, 104.3 mL, 0.682 mol), and 1173 (2-hydroxy-2-methylpropiophenone; 2 wt %, 3.6 mL) were added to the UV reactor neat. The reaction mixture was vigorously stirred with internal illumination at room temperature for 3 hours. After this time, $^1$H NMR analysis showed complete consumption of the olefin content, but only an average of 2 free thiols per triglyceride. The remaining olefin content was consumed by cross-linking arising from 1,6-hexanedithiol reacting twice.

Example 2. Synthesis of HOSBO-HDT$_3$ 1,6-Hexandithiol and 1173 (2-hydroxy-2-methylpropiophenone; 2 wt %, 7.8 g) were combined and stirred vigorously. High oleic soybean oil (391.1 g, 444.86 mmol) was added to a liquid addition funnel, the reaction was illuminated, and the oil was added as a slow stream. The reaction was stirred with external illumination for 5 h. A visible lack of gel formation was noted compared to HOSBO-HDT$_2$, and GPC confirmed that the material was not dimeric. $^1$H NMR confirmed complete olefin consumption, with an average of 3 free thiols per triglyceride.

Example 3. Synthesis of HOSBO-HDT$_x$

High oleic soybean oil (5.0 g, 5.69 mmol), 1,6-hexanedithiol (1 eq, 0.870 mL, 5.69 mmol), and 1173 (2-hydroxy- 2-methylpropiophenone; 2 wt %, 90.3 μL) were added to the UV reactor neat. The reaction mixture was stirred with external illumination at room temperature. After 1 hour, $^1$H NMR analysis showed that 27% of the olefin content had been thiolized. After 3 hours, $^1$H NMR analysis showed that 42% of the olefin content had been thiolized. To prevent crosslinking from continued reactivity one the desired functionalization level is attained, the radical must be quenched.

Example 4. Synthesis of HOSBO-HDT-Bt 2,2'-Dithiobis-benzothiazole (75 g, 58.0 mmol) was suspended in dry chloroform (750 mL) and stirred vigorously at ambient temperature. HOSBO-HDT of Example 1 was dissolved in dry chloroform (750 mL) and added dropwise over 17 hours to the stirred 2,2'-dithiobis-benzothiazole suspension (a rate of 0.735 mL/min). Upon completion of addition, the reaction was stirred 1 hour more to ensure complete consumption of the thiol. After this time, the reaction mixture was condensed. Hexane was added, and the suspension was gently heated at 35° C. The hexane mixture was filtered through a pad of celite. The solvent was removed from the filtrate under vacuum, and the crude material was triturated with methanol (3×200 mL), decanting the methanol washes. The remaining residue was dissolved in minimal chloroform and hexane (~200 mL) was added to precipitate any remaining by-products. The mixture was filtered through celite and condensed to give the pure product (89.7 g, 95% yield). $^1$H NMR analysis confirmed the pure product, with a total of 2 benzothiazole moieties per glyceride.

Example 5. Mixing and Testing of Rubber Compounds

The rubber compounds were mixed in a 360 g Haake mixer, using 100 phr polyisoprene polymer, 80 phr carbon black, 0-20 phr oil, 0-23 phr HOSBO-HDT-Bt of Example 4, and 8.5-11.1 phr additives in the first stage. The first stage was mixed for 2 minutes at 160° C. The final stage of mixing used 0.5-1.5 phr sulfur and 2.25 phr curatives. Samples were cured at 160° C. for 20 minutes. Adjustments to oil, additive, and sulfur levels were made based on calculations to compensate for excesses of these materials as the experimental reactive oil (HOSBO-HDT-BT) levels were varied.

TABLE 1

| Stage 1-2 min, 160° C. | |
|---|---|
| Polymer | 100 phr |
| CB | 80 phr |
| Oil | 0-31.5 phr |
| Additives | 8.5-11.1 phr |
| Stage 2 | |
| Sulfur | 0-1.5 phr |
| Curatives | 2.25 phr |

RPA, MDR, tensile, and extraction data were obtained on the samples. Cryo-milled compound samples were extracted by Accelerated Solvent Extraction (ASE) using acetone. Composition of the extracted residues was confirmed by NMR. The relevant data is reported in the following tables.

TABLE 2

| RPA & MDR Data | | | | |
|---|---|---|---|---|
| HOSBO-HDT-Bt | — | 6.86 | 14.3 | 22.88 |
| Oil | 20.0 | 14.0 | 7.50 | — |
| Additives | 11.1 | 10.52 | 9.89 | 8.63 |
| Sulfur | 1.50 | 1.22 | 0.910 | 0.550 |
| T90 | 2.69 | 3.57 | 5.38 | 10.4 |
| S' max | 14.0 | 17.0 | 19.4 | 20.5 |
| Δ torque | 12.2 | 14.9 | 17.2 | 17.9 |
| Uncured G' (0.833 Hz) | 119 | 134 | 150 | 173 |
| Tensile Data | | | | |
| TS5 | 1.96 | 2.31 | 3.05 | 5.43 |
| Elongation at break | 486 | 433 | 426 | 456 |
| M100 | 2.33 | 3.25 | 3.69 | 3.99 |
| M300 | 10.9 | 12.6 | 12.9 | 12.6 |

TABLE 3

| Extraction Data | |
|---|---|
| Extracted HOSBO-HDT-Bt (%) | 15.7 |
| Retained HOSBO-HDT-Bt (%) | 84.3 |

Significance

The above data demonstrates the utility of the benzothiazole disulfide-functionalized soybean oil. By using HOSBO-HDT-Bt, the uncured G', or stiffness, of the compound increases slightly, but remains well within processing capabilities, thus allowing for necessary mixing, extruding, and other manufacturing requirements. When the compound is cured, the benzothiazole disulfide moiety reacts, allowing the soybean oil to become part of the compound matrix, thereby removing it as a free oil from the compound. This stiffens the final compound, as exhibited by the drastically increased values for $S'_{max}$ and delta torque. Therefore, this novel oil allows access to much stiffer final compounds without sacrificing processability, which is a common problem plaguing manufacturers wanting extremely stiff final compounds. Typically, compounds with such great stiffness would exhibit much worse tensile properties, particularly a drop in their exhibited elongation at break. This tradeoff can be overcome by adjusting the curatives used in the compound. As shown above, despite having an extremely high $S'_{max}$, the compounds using HOSBO-HDT-Bt retain an elongation at break similar to that of the control compound. Therefore, use of this functional oil expands manufacturer and compounder access to much stiffer final compounds, while maintaining other desirable properties (uncured G' and tensile).

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A vegetable oil derivative comprising the structure

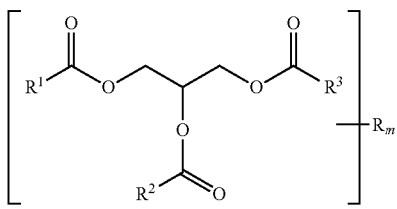

where $R^1$, $R^2$, and $R^3$ are independently C15-C20 alkenyl, C15-C20 alkyl, and optionally containing aromatic groups; R is —S—S—$R^4$ or R is —S—X—S—S—$R^4$ where X is an unsubstituted alkane diyl; $R^4$ is a monovalent organic group selected from the following structures:

where Z is a group that helps control the reactivity of the thiocarbonylthio moiety;

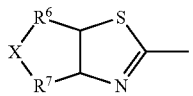

where X is selected from a group consisting of methylene units; $R^6$, $R^7$ can be independently hydrogen, alkyl chains, or aromatic moieties;

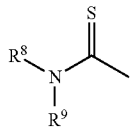

where $R^8$, $R^9$ can be independently alkyl or aromatic functionalities;

$R^{10}$— where $R^{10}$ is a non-substituted aromatic heterocycle;

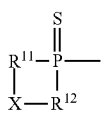

where X is selected from a group consisting of methylene units; $R^{11}$, $R^{12}$ can be symmetric or asymmetric and independently be an alkyl, aromatic, or ethereal substituents;

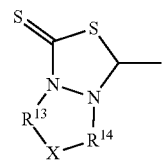

where X is selected from a group consisting of methylene units; $R^{13}$, $R^{14}$ can be symmetric or asymmetric and are independently hydrogen, an alkyl chain, aromatic containing functional group; and

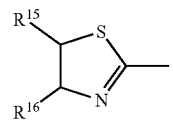

where $R^{15}$, $R^{16}$ can be independently hydrogen, alkyl chains, or aromatic moieties; each R is covalently bonded to a carbon atom of one of $R^1$, $R^2$, or $R^3$; and m is the number of R groups and is greater than (>) 1.

2. The vegetable oil derivative of claim 1 wherein $R^4$ is a sulfur-containing group capable of accelerating sulfur vulcanization.

3. The vegetable oil derivative of claim 1 wherein the vegetable oil is selected from the group consisting of soybean oils, canola oils, castor oils, palm oils, coconut oil, and corn oils.

4. The vegetable oil derivative of claim 1 wherein the vegetable oil is a high oleic soybean oil comprising about 75 percent by weight oleic acid residues.

5. The vegetable oil derivative of claim 3 wherein $R^1$, $R^2$, and $R^3$ together comprise about 75 weight percent oleyl groups.

6. A vulcanizable rubber composition comprising the vegetable oil derivative of claim 1.

7. A vulcanizable rubber composition comprising the vegetable oil derivative of claim 3.

8. A pneumatic tire comprising the vulcanizable rubber composition of claim 1.

9. A manufactured item comprising the vulcanizable rubber composition of claim 1 wherein the manufactured item is selected from the group consisting of tire treads, shoes, shoe soles, transmission belts, hoses, airsprings, conveyor belts, track belts, and vibration isolators.

10. A method of making a vegetable oil derivative of claim 1 comprising the steps of:
   obtaining a thiolized triglyceride; and
   reacting the thiolized triglyceride with a disulfide comprising a functional group at one terminus and a leaving group at the other terminus, to produce the vegetable oil derivative.

11. The method of claim 10, wherein the thiolized triglyceride is of the formula

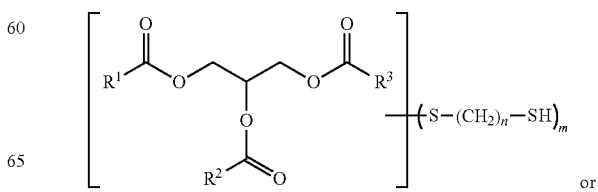

or

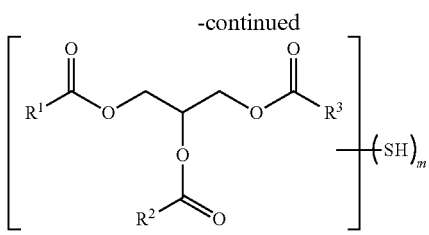

where $R^1$, $R^2$, and $R^3$ are independently C15-C20 alkenyl, C15-C20 alkyl, and optionally containing aromatic groups; each —S—$(CH_2)_n$—SH or —SH is covalently bonded to a carbon atom of one of $R^1$, $R^2$ or $R^3$; and m is the number of —S—$(CH_2)_n$—SH or —SH groups and is greater than (>) 1.

12. The method of claim 10 wherein the disulfide is of formula $$R^4—S—S—R^5$$

wherein the disulfide is symmetric or asymmetric; $R^5$ is an organic leaving group, and $R^4$ may be any monovalent organic group.

13. The method of claim 12 wherein $R^4$ is a mercaptobenzothiazolyl group or a thiuram group.

14. The method of claim 12 wherein $R^4$ is selected from the following structures:

where Z is a group that helps control the reactivity of the thiocarbonylthio moiety;

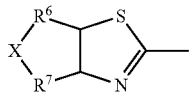

where X is selected from a group consisting of methylene units; $R^6$, $R^7$ can be independently hydrogen, alkyl chains, or aromatic moieties;

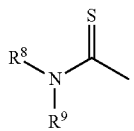

where $R^8$, $R^9$ can be independently alkyl or aromatic functionalities;

$R^{10}$— where $R^{10}$ is a non-substituted aromatic heterocycle;

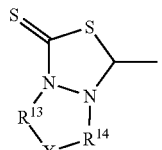

where X is selected from a group consisting of methylene units; $R^{11}$, $R^{12}$ can be symmetric or asymmetric and independently be an alkyl, aromatic, or ethereal substituents;

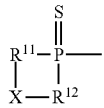

where X is selected from a group consisting of methylene units; $R^{13}$, $R^{14}$ can be symmetric or asymmetric and are independently hydrogen, an alkyl chain, aromatic containing functional group; and

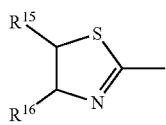

where $R^{15}$, $R^{16}$ can be independently hydrogen, alkyl chains, or aromatic moieties.

15. The method of claim 10 wherein the triglyceride is a vegetable oil selected from the group consisting of soybean oils, canola oils, castor oils, palm oils, coconut oil, and corn oils.

16. The method of claim 10, wherein the triglyceride is a high oleic soybean oil comprising about 75 percent by weight of oleic acid residues.

17. The method of claim 10, wherein the disulfide is a mercaptobenzothiazole disulfide or a thiuram disulfide.

* * * * *